US012752216B2

(12) United States Patent
Silva et al.

(10) Patent No.: US 12,752,216 B2
(45) Date of Patent: Oct. 6, 2026

(54) HEAT INTEGRATION VIA HEAT PUMP ON BOTTOM DIVIDING WALL COLUMN

(71) Applicant: SULZER MANAGEMENT AG, Winterthur (CH)

(72) Inventors: Michael Silva, Houston, TX (US); Saurav De, Katy, TX (US); Gary R. Martin, Grapevine, TX (US)

(73) Assignee: SULZER MANAGEMENT AG, Winterthur (CH)

( * ) Notice: Subject to any disclaimer, the term of this patent is extended or adjusted under 35 U.S.C. 154(b) by 40 days.

(21) Appl. No.: 17/926,252

(22) PCT Filed: May 17, 2021

(86) PCT No.: PCT/EP2021/062926

§ 371 (c)(1),
(2) Date: Nov. 18, 2022

(87) PCT Pub. No.: WO2021/233801

PCT Pub. Date: Nov. 25, 2021

(65) Prior Publication Data

US 2023/0201740 A1 Jun. 29, 2023

Related U.S. Application Data

(60) Provisional application No. 63/027,440, filed on May 20, 2020.

(51) Int. Cl.
*B01D 3/14* (2006.01)
*B01D 1/28* (2006.01)
(Continued)

(52) U.S. Cl.
CPC ........... *B01D 3/141* (2013.01); *B01D 1/2856* (2013.01); *B01D 3/007* (2013.01); *C07C 7/04* (2013.01);
(Continued)

(58) Field of Classification Search
CPC .... C07C 7/04; C07C 7/05; C07C 7/08; B01D 3/141; B01D 3/007
See application file for complete search history.

(56) References Cited

U.S. PATENT DOCUMENTS 6,077,985 A * 6/2000 Stork .................. B01D 1/2856 203/99
9,550,133 B2 * 1/2017 Favilli .................... B01D 3/007
(Continued)

FOREIGN PATENT DOCUMENTS

CN 106699552 A * 5/2017
CN 106748758 A * 5/2017
WO WO-2018114695 A1 * 6/2018 ........... B01D 1/2856

OTHER PUBLICATIONS

Shenyao Feng, Qing Ye, Hui Xia, Rui Li, Xiaomeng Suo, Integrating a vapor recompression heat pump into a lower partitioned reactive dividing-wall column for better energy-saving performance, Chemical Engineering Research and Design, vol. 125, 2017, pp. 204-213, https://doi.org/10.1016/j.cherd.2017.07.017.*
(Continued)

*Primary Examiner* — Jonathan Luke Pilcher
(74) *Attorney, Agent, or Firm* — Spencer Fane LLP

(57) ABSTRACT

A dividing wall column system is provided. The dividing wall column system comprises a dividing wall column, a first reboiler, a second reboiler, and a heat pump. The dividing wall column includes a dividing wall positioned in a bottom section of the dividing wall column to divide the bottom section of the dividing wall column into a first side and a second side. The first reboiler is outside of the dividing
(Continued)

wall column and in fluid communication with the first side of the bottom section of the dividing wall column. The second reboiler is outside of the dividing wall column and in fluid communication with the second side of the bottom section of the dividing wall column. The heat pump is in fluid communication with the dividing wall column and the second reboiler and configured to compress a first portion of an overhead product from the dividing wall column.

13 Claims, 1 Drawing Sheet

(51) Int. Cl.

| | |
|---|---|
| ***B01D 3/00*** | (2006.01) |
| ***C07C 7/04*** | (2006.01) |
| ***C10G 7/00*** | (2006.01) |
| *C07C 9/10* | (2006.01) |
| *C07C 9/12* | (2006.01) |
| *C07C 9/18* | (2006.01) |

(52) U.S. Cl.
CPC .................. *C10G 7/00* (2013.01); *C07C 9/10* (2013.01); *C07C 9/12* (2013.01); *C07C 9/18* (2013.01)

(56) References Cited

U.S. PATENT DOCUMENTS

| | | | | |
|---|---|---|---|---|
| 11,040,929 | B2 * | 6/2021 | Kim ......................... | C10G 7/08 |
| 2013/0267751 | A1 * | 10/2013 | Favilli ....................... | C07C 7/04<br>422/187 |

OTHER PUBLICATIONS

Editor(s): James R. Couper, W. Roy Penney, James R. Fair, Stanley M. Walas, "Chemical Process Equipment (Revised Second Edition)", Chapter 18: "Process Vessels", Gulf Professional Publishing, 2010, pp. 641-661, ISBN 9780123725066, https://doi.org/10.1016/B978-0-12-372506-6.00015-0.*

Long Nguyen Van Duc et al.; "Design and optimization of heat integrated dividing wall columns for improved debutanizing and deisobutanizing fractionation of NGL"; Korean Journal of Chemical Engineering; c. Feb. 2013; vol. 30, No. 2; pp. 286-294 (XP055831863).

Aurengzeb Md et al; "Vapor recompression with interreboiler n a ternary dividing wall column: Improving energy efficiency and savings, and economic performance"; Applied Thermal Engineering; c. Jan. 2019; vol. 147; pp. 1009-1023 (XP055831897).

International Preliminary Report on Patentability issued Aug. 18, 2022 in corresponding International Application PCT/EP2021/062926.

International Search Report and Written Opinion issued Aug. 20, 2021 in corresponding International Application PCT/EP2021/062926.

* cited by examiner

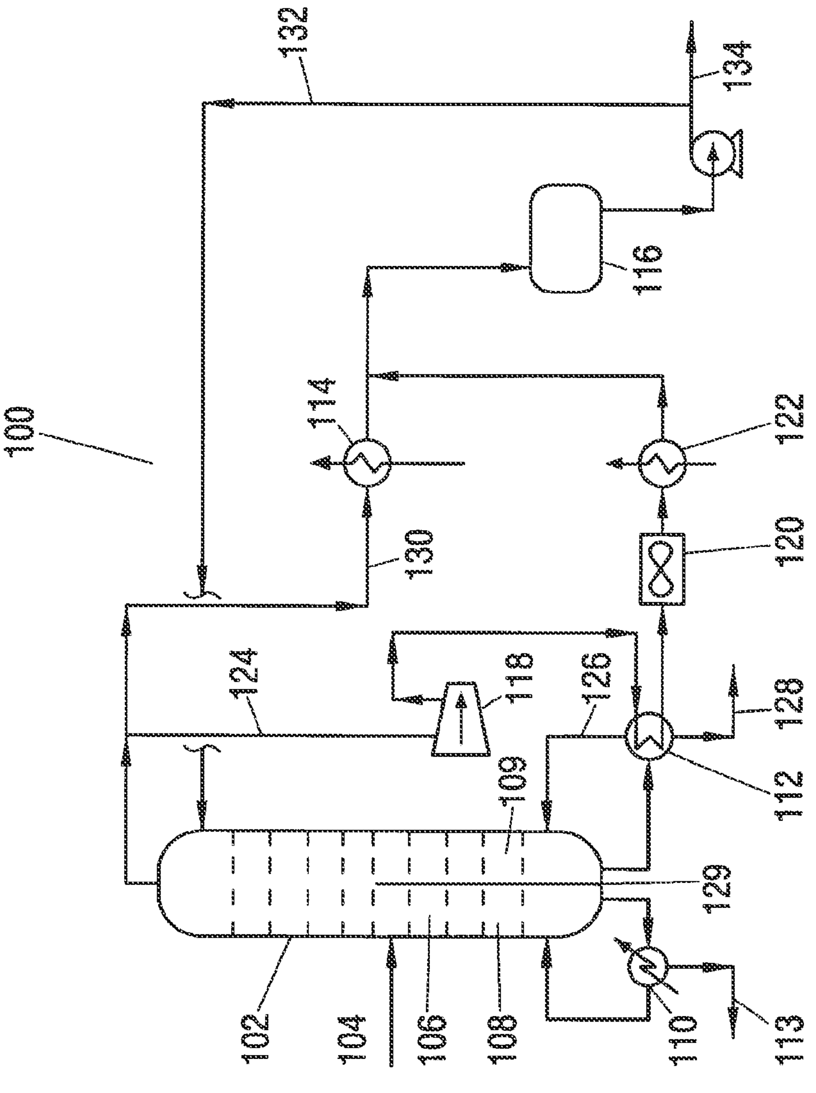
100
102
104
106
108
109
110
112
113
114
116
118
120
122
124
126
128
129
130
132
134

HEAT INTEGRATION VIA HEAT PUMP ON BOTTOM DIVIDING WALL COLUMN

CROSS-REFERENCE TO RELATED APPLICATION

This application is a U.S. National Stage application of International Application No. PCT/EP2021/062926, filed May 17, 2021, which claims priority to U.S. Provisional Application No. 63/027,440, filed May 20, 2020, the contents of each of which are hereby incorporated by reference.

BACKGROUND

Technical Field

The present disclosure relates to a dividing wall column system particularly for use in a de-isopentanizer (DIP) or de-isobutanizer (DIB) application. The present disclosure further relates to a method for producing an iso-$C_4$-hydrocarbon composition from a hydrocarbon feed.

Background Information

DIPs and DIBs are typically part of a Natural Gas Liquid (NGL) fractionation plant. NGL fractionation configurations are typically made up of a series of columns that distill the lighter component in each successive column. For example, if fractionating hydrocarbon molecules from $C_1$_$C_{5+}$, the following columns may be used: demethanizer column, deethanizer column, depropanizer column, and a debutanizer column. Additional columns such as DIPs or DIBs may be added to further fractionate a particular component into its paraffinic and iso-paraffinic components. More specifically, in a typical NGL fractionation train, a debutanizer column produces a distillate with a mixture of n-butane and isobutane, and this distillate is then fed to a DIB column, in which i-$C_4$ and n-$C_4$-hydrocarbon fractions are separated. With so many columns and reboilers in the configuration, there are strategic spots to include heat integration to help in the overall utility usage of the plant.

The object underlying the present disclosure is to provide a dividing wall column system particularly for use in a DIP or DIB application and to provide a method for producing an iso-$C_4$-hydrocarbon composition from a hydrocarbon feed, wherein the method and system are energy efficient, i.e. the system requires comparable low investment costs and the method has comparable low operational costs, but with both, the system and the method nevertheless having a very high separation efficiency.

SUMMARY

In accordance with the present disclosure, this object is satisfied by providing a dividing wall column system comprising: a dividing wall column comprising a dividing wall positioned in a bottom section of the dividing wall column to divide the bottom section of the dividing wall column into a first side and a second side, a first reboiler outside of the dividing wall column and in fluid communication with the first side of the bottom section of the dividing wall column, a second reboiler outside of the dividing wall column and in fluid communication with the second side of the bottom section of the dividing wall column, and a heat pump in fluid communication with the dividing wall column and the second reboiler, the heat pump being configured to compress a first portion of the overhead product from the dividing wall column.

It has been found by the inventors of the present disclosure that by using a dividing wall column comprising a dividing wall positioned in the bottom section of the dividing wall column to divide the bottom section of the dividing wall column into a first side and a second side, i.e. by using a bottom dividing wall column, which is in fluid communication with a heat pump, wherein the heat pump is also in fluid communication with the second reboiler so that a first portion of the overhead product (or light product respectively) of the dividing wall column is compressed in the heat pump and then fed to the second reboiler in order to heat at least a portion of the bottom product withdrawn from the second side of the bottom section of the bottom dividing wall column, the energy consumption of the dividing wall column system, in particular when used as a de-isopentanizer or a de-isobutanizer, may be drastically decreased, but nevertheless an very high separation efficiency is obtained. The vapor generated in the first reboiler is used to strip the teed on the first side of the bottom section defined by the dividing wall of $C_4$-hydrocarbon material, which produces a $C_{5+}$-hydrocarbon product on that side of the bottom section of the dividing wall column. Conversely, the vapor generated in the second reboiler is used to strip i-$C_4$-hydrocarbons to the top of the dividing wall column. All in all, according to the present disclosure, the overhead product or vapor, respectively, produced by the dividing wall column is used to heat the second side or $C_4$-reboiler, respectively. Only a portion of the overhead vapor stream is used and preferably the bottom dividing wall column further includes one overhead condenser and an accumulator for reflux of a portion of the overhead product. As such, the balance of overhead vapor will continue to a conventional overhead condenser before being collected in the preferred overhead accumulator arranged downstream of the second reboiler along with the condensed vapor that was used to heat the reboiler. The dividing wall column is typically operated at a pressure of less than 1 MPag. Therefore, the overhead vapor from this column is close to typical cooling water supply temperature ranges. As such, by condensing this vapor stream in the reboiler, cooling water requirements and heating medium requirements will be reduced. Thus, the present disclosure relates to a heat integration scheme that uses a heat pump to compress the overhead vapor obtained in the dividing wall column so as to increase its temperature to heat the second reboiler of the dividing wall column.

Heat pump means in the present disclosure any device that is able to compress the light product, i.e. the overheads product, of the bottom dividing wall column. Thus, the heat pump may comprise one or more compressors and may consist of one or more compressors. For instance, the heat pump may comprise or consist of one or more turbofans.

The second reboiler may be any kind of reboiler or heat exchanger, respectively. Examples therefore are plate and shell reboilers, compabloc heat exchangers, shell and tube reboilers and the like. For instance, the second reboiler is a shell and tube reboiler and the bottom product of the second side of the dividing wall column is transported through the shell side of the second reboiler, whereas the portion of the overhead product of the dividing wall column, which has been compressed in the heat pump, is transported through the tube of the second reboiler.

In accordance with the present disclosure, the dividing wall column is a bottom dividing wall column, i.e. a dividing wall column comprising a dividing wall positioned in the bottom section of the dividing wall column to divide the bottom section of the dividing wall column into a first side and a second side. The dividing wall extends preferably from the bottom of the dividing wall column over a part of the height of the dividing wall column at least essentially vertically upwards. Essentially vertically upwards may mean that the angle between the dividing wall and the length axis of the dividing wall column is at most 40°, preferably at most 20°, more preferably at most 10° and most preferably 0°, wherein the height of the dividing wall column is the straight distance between the top and the bottom of the dividing wall column. Such a bottom dividing wall column comprises two independent stripping sections on either side of the dividing wall (namely the first and second sides of the bottom section) and a common rectifying section in the top section above the dividing wall.

It is preferred that the dividing wall of the dividing wall column extends from the bottom of the dividing wall column, seen from the bottom to the top of the dividing wall column, over 10 to 80%, more preferably over 10 to 70%%, yet more preferably over 20 to 70%, even more preferably over 30 to 70%, and most preferably over 40 to 60%, of the height of the dividing wall column. The bottom section is that part of the dividing wall column in which the dividing wall is located, and the bottom section defines the first and second sides, whereas the top section is the part of the dividing wall column above the dividing wall.

The dividing wall column may comprise at least one internal element selected from the group consisting of: trays, structured packings, random packings and combinations of two or more of the aforementioned elements, in order to improve its mass and heat transfer efficiency. In addition, where necessary distributors and collectors may be included above and below the one or more internal elements.

In a further development of the idea of the present disclosure, it is proposed that the dividing wall column system further comprises a first condenser, which is in fluid communication with the second reboiler, i.e. the dividing wall column system further comprises a line or conduit, respectively, between the second reboiler and the first condenser.

In accordance with a further embodiment of the present disclosure, the second reboiler is fluidly coupled to the dividing wall column to feed-reflux to the second side of the dividing wall column. This means that preferably the second reboiler comprises a line connecting the second side of the bottom section of the dividing wall column with the second reboiler so as to feed during the operation bottom product from the second side of the bottom section of the dividing wall column into the second reboiler and a further line connecting the second reboiler with the second side of the bottom section of the dividing wall column so as to feed during the operation bottom product from the second reboiler back into the second side of the bottom section of the dividing wall.

Preferably, the first reboiler is also fluidly coupled to the dividing wall column to feed-reflux to the first side of the dividing wall column, i.e. the first reboiler comprises a line connecting the first side of the bottom section of the dividing wall column with the first reboiler so as to feed during the operation bottom product from the first side of the bottom section of the dividing wall column into the first reboiler and a further line connecting the first reboiler with the first side of the bottom section of the dividing wall column so as to feed during the operation bottom product from the first reboiler back into the first side of the bottom section of the dividing wall.

Moreover, it is preferred that the dividing wall column system further comprises a second condenser in fluid communication with the dividing wall column and configured to receive a second portion of the overhead product from the dividing wall column. In other words, it is preferred that the dividing wall column system further comprises a second condenser which is connected with the overhead of the dividing wall column by a line or conduit, respectively. This second portion of the overhead product is not led over the heat pump In a further development of the idea of the present disclosure, it is suggested that the dividing wall column system further comprises an accumulator in fluid communication with the first and second condensers. Thus, preferably a first line or conduit, respectively, connects the accumulator with the first condenser and a second line or conduit, respectively, connects the accumulator with the second condenser.

Preferably, in the aforementioned embodiment of the present disclosure, the accumulator is in fluid communication with the dividing wall column to feed-reflux to the dividing wall column, i.e. a recirculation line connects the accumulator with the dividing wall column. Preferably, the recirculation line is connected with the top section or overhead of the dividing wall column.

In accordance with a further embodiment of the present disclosure, a third condenser is arranged downstream of the first condenser and in fluid communication with the first condenser.

According to a further aspect, the present disclosure relates to a method of producing an i-$C_4$-hydrocarbon product, which is performed in the aforementioned dividing wall column system.

More specifically, the method comprises the steps of:

introducing a feed containing hydrocarbons to the dividing wall column of the aforementioned dividing wall column system;

feeding, from the first side of the dividing wall column, a bottom product comprising $C_{5+}$-hydrocarbons to the first reboiler;

feeding, from the second side of the dividing wall column, a bottom product comprising n-$C_4$-hydrocarbons to the second reboiler;

feeding a first portion of the overhead product from the dividing wall column to the heat pump and compressing the first portion of the overhead product therein to form a compressed overhead product; and feeding the compressed overhead product from the heat pump to the second reboiler to exchange heat between the compressed overhead product and the bottom product comprising n-$C_4$-hydrocarbons.

Preferably, a portion of the bottom product comprising n-$C_4$-hydrocarbons is fed as a reflux stream from the second reboiler to the second side of the bottom section of the dividing wall column, whereas the other part of the bottom product comprising n-$C_4$-hydrocarbons is withdrawn from the dividing wall column system.

Likewise, it is preferred that a portion of the bottom product comprising $C_{5+}$-hydrocarbons is fed as a reflux stream from the first reboiler to the first side of the bottom section of the dividing wall column, whereas the other part of the bottom product comprising $C_{5+}$-hydrocarbons is withdrawn from the dividing wall column system.

In a further development of the idea of the present disclosure, it is proposed that the method further comprises the step of feeding the compressed overhead product from the second reboiler, after it has heat exchanged in the second reboiler with the bottom product comprising n-$C_4$-hydrocarbons, to a first condenser arranged downstream of the second reboiler, and cooling or condensing the bottom product comprising n-$C_4$-hydrocarbons in the first condenser.

It is preferred in the aforementioned embodiment that the dividing wall column system further comprises an accumulator and that the overhead product is fed from the first condenser to the accumulator. Alternatively, between the first condenser and the accumulator, a further condenser may be arranged so as to further cool or condense the bottom product comprising n-$C_4$-hydrocarbons therein.

In accordance with a further embodiment of the present disclosure, the method further comprises the step of leading a reflux stream from the accumulator to the dividing wall column and in particular into the top section or overhead of the dividing wall column.

It is further preferred that the dividing wall column system further comprises a second condenser and that, in addition to the first portion of the overhead product being fed into the heat pump, a second portion of the overhead product is fed from the dividing wall column to the second condenser so as to at least partially condense the overhead product therein.

In a further development of the idea of the present disclosure, it is suggested that in the aforementioned embodiment the second portion of the overhead product, which has been preferably at least partially condensed in the second condenser, is fed to the accumulator.

The method may further comprise the step of producing an i-C4-hydrocarbon feed in the accumulator.

BRIEF DESCRIPTION OF THE DRAWINGS

The disclosure will be explained in more detail hereinafter with reference to the drawings.

FIG. 1 illustrates a bottom dividing wall column system with a heat pump in accordance with an embodiment of the present disclosure.

DETAILED DESCRIPTION

Various aspects will now be described more fully with reference to the accompanying drawing. The disclosure may, however, be embodied in many different forms and should not be construed as limited to the aspects set forth herein.

FIG. 1 illustrates a bottom dividing wall column system 100 according to an embodiment of the present disclosure. The system 100 includes a dividing wall column 102 that receives a feed 104 that includes hydrocarbons. The dividing wall column 102 includes a bottom dividing wall 106 that divides the bottom section of the dividing wall column 102 into two sides 108, 109. The bottom dividing wall 106 extends vertically from the bottom of the dividing wall column 102 upwardly over about 50% of the height of the dividing wall column 102. Furthermore, the dividing wall column system 100 includes a first reboiler 110 and a second reboiler 112 that are fluidly coupled to sides 108, 109 of the bottom sections of the dividing wall column 102 respectively. The second reboiler 112 is embodied as a shell and tube reboiler. The first reboiler 110 strips the feed on the first side 108 of the dividing wall 106 of $C_4$-hydrocarbons and produces a $C_{5+}$-product stream on that first side 108 of the dividing wall 106, which is withdrawn from the dividing column system 100 via the $C_{5+}$-hydrocarbon product line 113. The second reboiler 112 strips i-$C_4$-hydrocarbons and produces a n-$C_4$-hydrocarbon product stream. In addition, the bottom dividing wall column system 100 comprises a compressor 118 (or heat pump, respectively), a first condenser 120, a second condenser 114, a third condenser 122 and an (overhead) accumulator 116.

The dividing wall column 102 outputs an overhead product (or light product, respectively) at the top of the dividing wall column. A first portion of the overhead product is fed via line 124 to the compressor 118, where it is compressed. The compressed overhead product is then fed into the tube side of the second reboiler 112, whereas the bottom product withdrawn from the bottom section of the dividing wall column 102 is fed into the shell of the second reboiler 112 so that a heat exchange between the warmer compressed overhead product and the colder bottom product is effected, which leads to an at least partial vaporization of the n-$C_4$-hydrocarbon bottom product obtained in the second side 109 of the bottom section of the dividing wall column 102. While a portion of the n-$C_4$-hydrocarbon bottom product is refluxed from the shell of the second reboiler 112 via the reflux line 126 back into the bottom section of the dividing wall column 102, the other portion of the n-$C_4$-hydrocarbon bottom product is withdrawn from the dividing column system 100 via the n-$C_4$-hydrocarbon product line 128. Alternatively, a part of or all of the n-$C_4$-hydrocarbon product stream may be withdrawn from the column sump 129 instead of from the reboiler 112. The compressed overhead product is fed from the tube side of the second reboiler 112 to the first condenser 120, from there to the third condenser 122, and from there into the accumulator 116.

The second portion of the overhead product is fed via line 130 directly, i.e. under bypassing the compressor 118, to the second condenser 114 and from there to the accumulator 116, where it is combined with the first portion of the overhead product which has been led through the compressor 118 and through the second reboiler 112. From the accumulator 116, a portion of the i-$C_4$-hydrocarbon overhead product is recycled via reflux line 132 into the top section of the dividing wall column 102, whereas the other portion of the i-$C_4$-hydrocarbon overhead product is withdrawn from the dividing column system 100 via the i-$C_4$-hydrocarbon product line 134.

The dividing wall column 102 is typically operated at a pressure of less than 1 MPag. The light product (i.e. overhead vapor) from dividing wall column 102 is close to typical cooling water supply temperature ranges. As such, by condensing the light product in reboiler 112, cooling water requirements and heating medium requirements are reduced.

The benefits of bottom dividing wall column system 100 include:

- Reduction in overhead condensing duty, thereby requiring less cooling water supply.
- Reduction in hot medium requirement (typically hot oil/steam) for the n-$C_4$-reboiler.
- Savings in operating costs.
- Smaller footprint of the hot oil system due to a lower requirement of hot oil.
- Lower heater emissions due to lower hot oil requirement.

The invention claimed is:

1. A dividing wall column system comprising:

a dividing wall column comprising a dividing wall positioned in a bottom section of the dividing wall column and extending from a bottom of the dividing wall column over only a part of a height of the dividing wall column at least essentially vertically upwards such that that an angle between the dividing wall and a length axis of the dividing wall column is at most 40° to divide the bottom section of the dividing wall column into a first side and a second side;

a first reboiler outside of the dividing wall column and in fluid communication with the first side of the bottom section of the dividing wall column;

a second reboiler outside of the dividing wall column and in fluid communication with the second side of the bottom section of the dividing wall column;

a heat pump in fluid communication with the dividing wall column and the second reboiler and configured to compress a first portion of an overhead product from the dividing wall column;

a first condenser in fluid communication with a tube side of the second reboiler and configured to receive and cool the compressed first portion of the overhead product;

a second condenser in fluid communication with the dividing wall column and configured to receive and condense a second portion of the overhead product that bypasses the heat pump; and a third condenser arranged downstream of and in fluid communication with the first condenser to further condense the compressed first portion of the overhead product.

2. The dividing wall column system of claim 1, wherein the second reboiler is fluidly coupled to the dividing wall column to feed-reflux to the second side of the dividing wall column and the first reboiler is fluidly coupled to the dividing wall column to feed-reflux to the first side of the dividing wall column.

3. The dividing wall column system of claim 1, further comprising an accumulator in fluid communication with the first condenser and the second condenser.

4. The dividing wall column system of claim 3, wherein the accumulator is in fluid communication with the dividing wall column to feed-reflux to the dividing wall column.

5. A method of producing an i-$C_4$-hydrocarbon product, the method comprising:

introducing a feed containing hydrocarbons to the dividing wall column of the dividing wall column system in accordance with claim 1;

feeding, from the first side of the dividing wall column, a bottom product comprising $C_{5+}$-hydrocarbons to the first reboiler;

feeding, from the second side of the dividing wall column, a bottom product comprising n-$C_4$-hydrocarbons to the second reboiler;

feeding the first portion of the overhead product from the dividing wall column to the heat pump and compressing the first portion of the overhead product therein to form a compressed overhead product; and feeding the compressed overhead product from the heat pump to the second reboiler to exchange heat between the compressed overhead product and the bottom product comprising n-$C_4$-hydrocarbons.

6. The method of claim 5, wherein a reflux stream is fed from the second reboiler to the second side of the bottom section of the dividing wall column.

7. The method of claim 5, wherein a reflux stream is fed from the first reboiler to the first side of the bottom section of the dividing wall column.

8. The method of claim 5, further comprising feeding the compressed overhead product from the second reboiler to a first condenser and condensing it therein to form a condensed overhead product.

9. The method of claim 8, wherein the dividing wall column system further comprises an accumulator, further comprising feeding the condensed overhead product from the first condenser to the accumulator.

10. The method of claim 5, wherein the dividing wall column system further comprises a second condenser, further comprising feeding a second portion of the overhead product from the dividing wall column to the second condenser.

11. The method of claim 10, further comprising feeding the second portion of the overhead product to the accumulator.

12. The method of claim 11, further comprising producing an i-$C_4$-hydrocarbon feed from the accumulator.

13. The method of claim 12, further comprising leading a reflux stream from the accumulator to the dividing wall column.

* * * * *